United States Patent
Tachikawa et al.

(10) Patent No.: US 9,415,169 B2
(45) Date of Patent: Aug. 16, 2016

(54) GASKET AND SYRINGE

(75) Inventors: Kouichi Tachikawa, Yamanashi-ken (JP); Junichi Ogawa, Yamanashi-ken (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1349 days.

(21) Appl. No.: 13/255,289

(22) PCT Filed: Feb. 23, 2010

(86) PCT No.: PCT/JP2010/052769
§ 371 (c)(1),
(2), (4) Date: Oct. 5, 2011

(87) PCT Pub. No.: WO2010/103919
PCT Pub. Date: Sep. 16, 2010

(65) Prior Publication Data
US 2012/0016314 A1    Jan. 19, 2012

(30) Foreign Application Priority Data
Mar. 9, 2009 (JP) ................................ 2009-055454

(51) Int. Cl.
*A61M 5/315* (2006.01)
*A61M 5/31* (2006.01)

(52) U.S. Cl.
CPC ... *A61M 5/31515* (2013.01); *A61M 2005/3104* (2013.01)

(58) Field of Classification Search
CPC ................. A61M 5/31515; A61M 2005/3104
USPC .......................... 604/181, 187, 218, 219, 228
See application file for complete search history.

(56) References Cited

U.S. PATENT DOCUMENTS 3,831,601 A * 8/1974 Kessell ............. A61M 5/31513
604/222
4,180,069 A    12/1979 Walters
(Continued)

FOREIGN PATENT DOCUMENTS

EP    0 998 952 A1    5/2000
JP    54-016885 A    2/1979
(Continued)

OTHER PUBLICATIONS

The extended European Search Report issued on Jul. 30, 2014, by the European Patent Office in corresponding European Patent Application No. 10750673.5-1662. (6 pages).
(Continued)

*Primary Examiner* — Emily Schmidt
*Assistant Examiner* — Lauren M Peng
(74) *Attorney, Agent, or Firm* — Buchanan Ingersoll & Rooney PC

(57) ABSTRACT

A gasket configured so that a pusher having a male screw thread on the outer periphery of its tip is connected to the gasket through the male screw thread and so that the gasket slides within a syringe outer tube when the pusher is operated in the longitudinal direction. The gasket includes: a gasket body having a hollow section and a female screw thread in the inner peripheral section of the hollow section engaged by the male screw thread; and projections on the outer peripheral section of the gasket body extending circumferentially of the outer peripheral section and axially arranged in spaced relation to each other. When the gasket is not yet inserted into the syringe outer tube, a screw thread located in a portion on the inner side of and in direct proximity to the projection has a smaller height than a screw thread located in the remaining portion.

11 Claims, 3 Drawing Sheets

(56) References Cited

U.S. PATENT DOCUMENTS

| | | | |
|---|---|---|---|
| 4,543,093 A * | 9/1985 | Christinger | 604/228 |
| 6,179,815 B1 * | 1/2001 | Foote | 604/181 |
| 2004/0099994 A1 | 5/2004 | Brinkhues | |

FOREIGN PATENT DOCUMENTS

| | | |
|---|---|---|
| JP | 2004-121344 A | 4/2004 |
| JP | 2004-525011 A | 8/2004 |
| JP | 2004-245322 A | 9/2004 |
| JP | 2005-080957 A | 3/2005 |
| JP | 2007-289677 | 11/2007 |
| WO | 01/97885 A1 | 12/2001 |

OTHER PUBLICATIONS

International Search Report (PCT/ISA/210) issued on Mar. 30, 2010, by Japanese Patent Office as the International Searching Authority for International Application No. PCT/JP2010/052769.

Written Opinion (PCT/ISA/237) issued on Mar. 30, 2010, by Japanese Patent Office as the International Searching Authority for International Application No. PCT/JP2010/052769.

* cited by examiner

GASKET AND SYRINGE

TECHNICAL FIELD

The present invention relates to a gasket and a syringe.

BACKGROUND ART

There has been known a syringe which can be filled with a medicinal liquid in a sterile manner (see, for example, Patent Document 1). The syringe disclosed in Patent Document 1 includes a syringe outer tube, a gasket contained in the syringe outer tube and slidable within the syringe outer tube, and a plunger connected to the gasket and operated to move the gasket, wherein a space surrounded by the syringe outer tube and the gasket is filled with a medicinal liquid. In the syringe according to Patent Document 1, the connection between the gasket and the plunger is accomplished through screw engagement. For this purpose, the gasket is formed with a female screw in an inner peripheral portion of the proximal end thereof, while the plunger is formed with a male screw on an outer peripheral portion of the distal end thereof. The screw threads of the female screw and the male screw are each uniform in height. In addition, the gasket has a plurality of projections which are projectingly formed on the outer peripheral portion of the gasket so as to extend along the circumferential direction and which are spaced from each other along the longitudinal direction of the gasket.

By filling the syringe configured as above with a medicinal liquid, a prefilled syringe can be produced. The prefilled syringe is produced in the following manner. First, an empty syringe outer tube having been sterilized is filled with the medicinal liquid under a sterile condition, and then the gasket is inserted into the syringe outer tube (first step). Next, the plunger rod is connected to the gasket, to complete the prefilled syringe (second step).

In the first step, the gasket is in a state in which each of the projections is pressed by the inner wall (inner peripheral surface) of the syringe outer tube. Therefore, at a portion of the female screw that corresponds to the projection (the portion which is located on the inner side of the gasket and in close proximity to the projection), the inside diameter is reduced, so that the height of the screw thread is increased. Upon transition to the second step under this condition in an attempt to connect the plunger rod to the gasket, engagement of the male screw of the plunger rod becomes difficult because of reduction in the inside diameter of the female screw of the gasket. Thus, there has been a problem that the connecting operation is not easy to carry out. Such a problem is generated particularly in the production of a prefilled syringe having a small-diameter syringe outer tube which has an inside diameter of 7 mm or less.

In order to solve this problem, it may be contemplated to reduce the height of the screw threads of the female screw in the gasket and the male screw on the plunger rod. In this case, however, a new problem is generated in that the force of screw engagement between the screw threads cannot be secured on such a level that the gasket will not be disengaged from the plunger rod when the plunger rod is operated.

Patent Document 1: Japanese Laid-Open Patent Publication No. 2007-289677

SUMMARY OF THE INVENTION

It is an object of the present invention to provide a gasket and a syringe which enable the connecting operation to be carried out easily at the time of connecting a pusher, and also enable secure connection with the pusher to be attained.

In order to attain the above object, according to the present invention, there is provided a gasket which is connected to a pusher having a male screw formed on an outer peripheral portion of a distal end thereof by screw engagement with the male screw of the pusher, the gasket being slid within a syringe outer tube by operation of the pusher in longitudinal directions thereof, the gasket including:

a gasket body having a hollow section and a female screw formed on an inner peripheral portion of the hollow section, the female screw being screw-engaged with the male screw; and a plurality of projections which are projectingly formed on an outer peripheral portion of the gasket body so as to extend in a circumferential direction of the outer peripheral portion and which are arranged so as to be spaced from each other along an axial direction of the gasket body, wherein in an uninserted state in which the gasket is not yet inserted into the syringe outer tube, a screw thread located at a portion on the inner side of the gasket and in close proximity to each of the projections has a smaller height than a screw thread located at another portion.

In addition, in the gasket according to the present invention, it is preferable that in an inserted state in which the gasket is inserted into the syringe outer tube, each of the projections is pressed by an inner peripheral surface of the syringe outer tube, so that height difference between the screw threads of the female screw approaches zero.

Further, in the gasket according to the present invention, preferably, the height difference between the screw threads of the female screw in the uninserted state is of 0.08 to 0.30 mm.

In addition, the gasket according to the present invention, preferably, is so configured that in the female screw in the uninserted state, the tooth thickness of the lower screw thread is larger than the tooth thickness of the higher screw thread.

Further, in the gasket according to the present invention, preferably, the female screw has a pitch of 1.0 to 4.0 mm.

In addition, the gasket according to the present invention, preferably, is so configured that in the uninserted state, the outside diameter of a portion of the gasket that has the projection is greater than the inside diameter of the syringe outer tube by 3 to 20%.

Besides, in the gasket according to the present invention, it is preferable that in the inserted state, a gap is formed between the female screw and the male screw.

In addition, in the gasket according to the present invention, preferably, the screw thread of the female screw is provided with a rounded portion at a crest thereof.

Besides, in the gasket according to the present invention, preferably, the number of the projections is two, and the two projections are disposed to be spaced from each other by a spacing distance of 1 to 10 mm.

In addition, in the gasket according to the present invention, preferably, the female screw is formed between the two projections.

Besides, in the gasket according to the present invention, preferably, the screw threads of the male screw on the pusher are uniform in height.

In order to attain the above object, according to the present invention, there is provided a syringe provided with the gasket according to the present invention, wherein the inside diameter of the syringe outer tube is equal to or less than 7 mm.

In order to attain the above object, according to the present invention, there is provided
a syringe including:
a gasket according to the present invention;
a syringe outer tube into which the gasket is inserted; and
a pusher formed with a male screw for engagement with the female screw of the gasket.

DESCRIPTION OF THE EMBODIMENTS

Now, a gasket and a syringe according to the present invention will be described in detail below, based on a preferred embodiment shown in the accompanying drawings.

Figure 1:
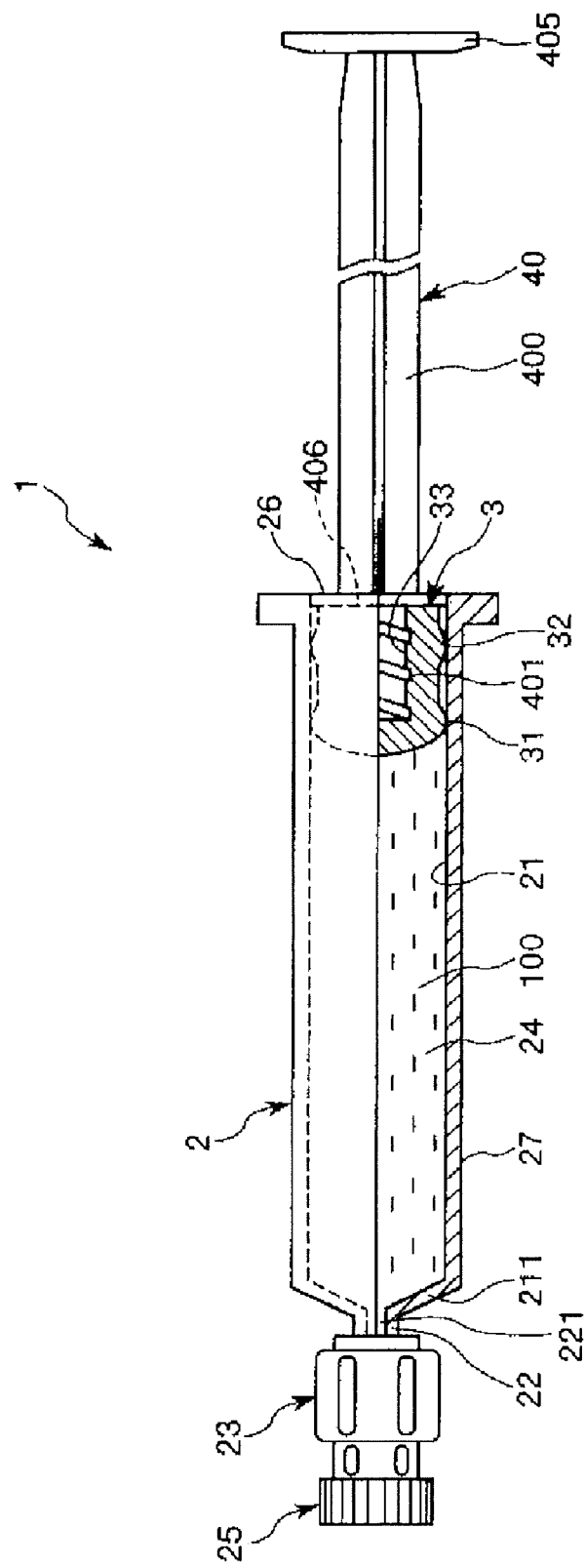
FIG. 1 is a partial longitudinal sectional view showing a case where a syringe according to the present invention is applied to a prefilled syringe.
Figure 2:
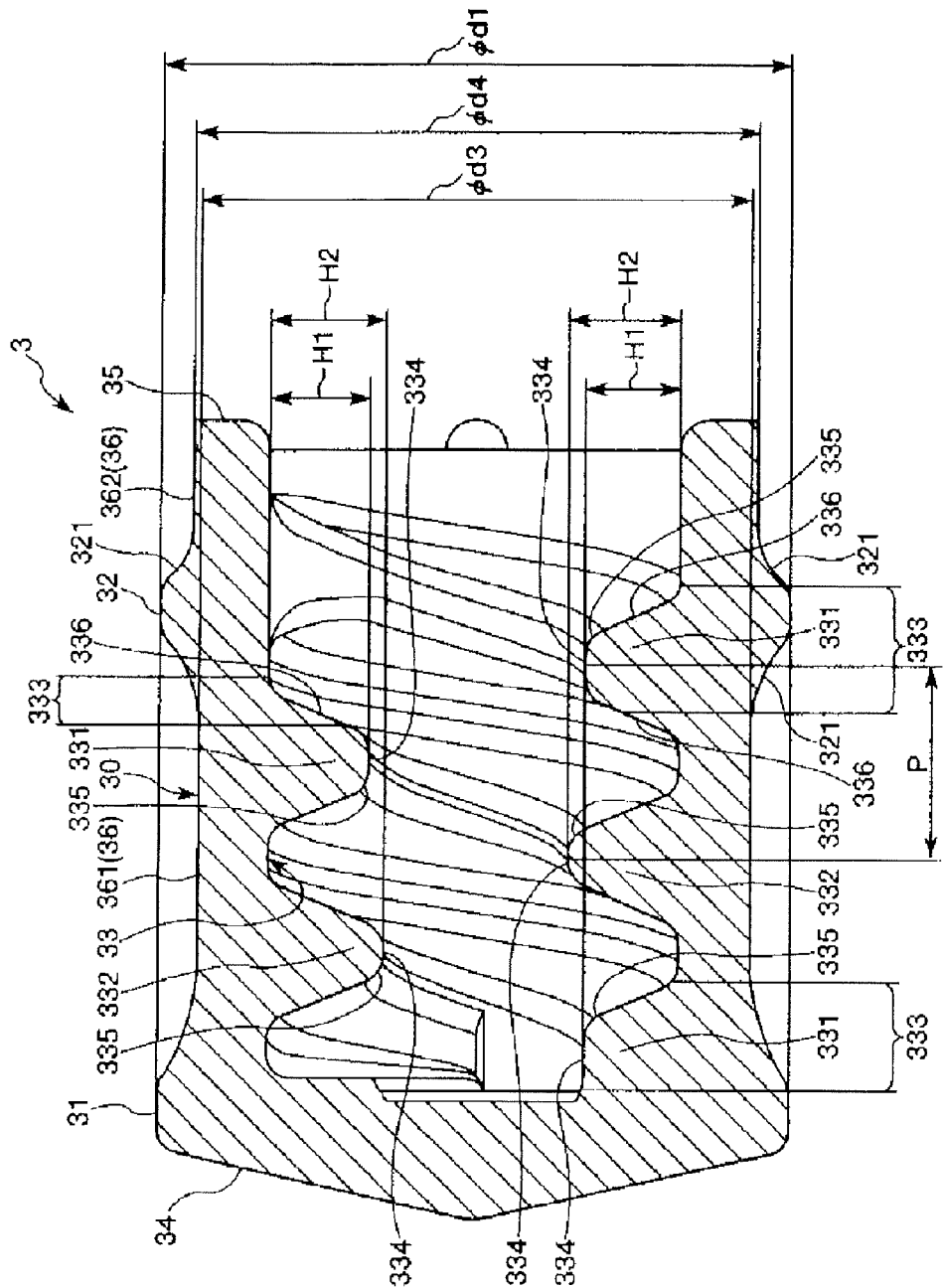
FIG. 2 is a longitudinal sectional view of a gasket according to the present invention, in an uninserted state.
Figure 3:
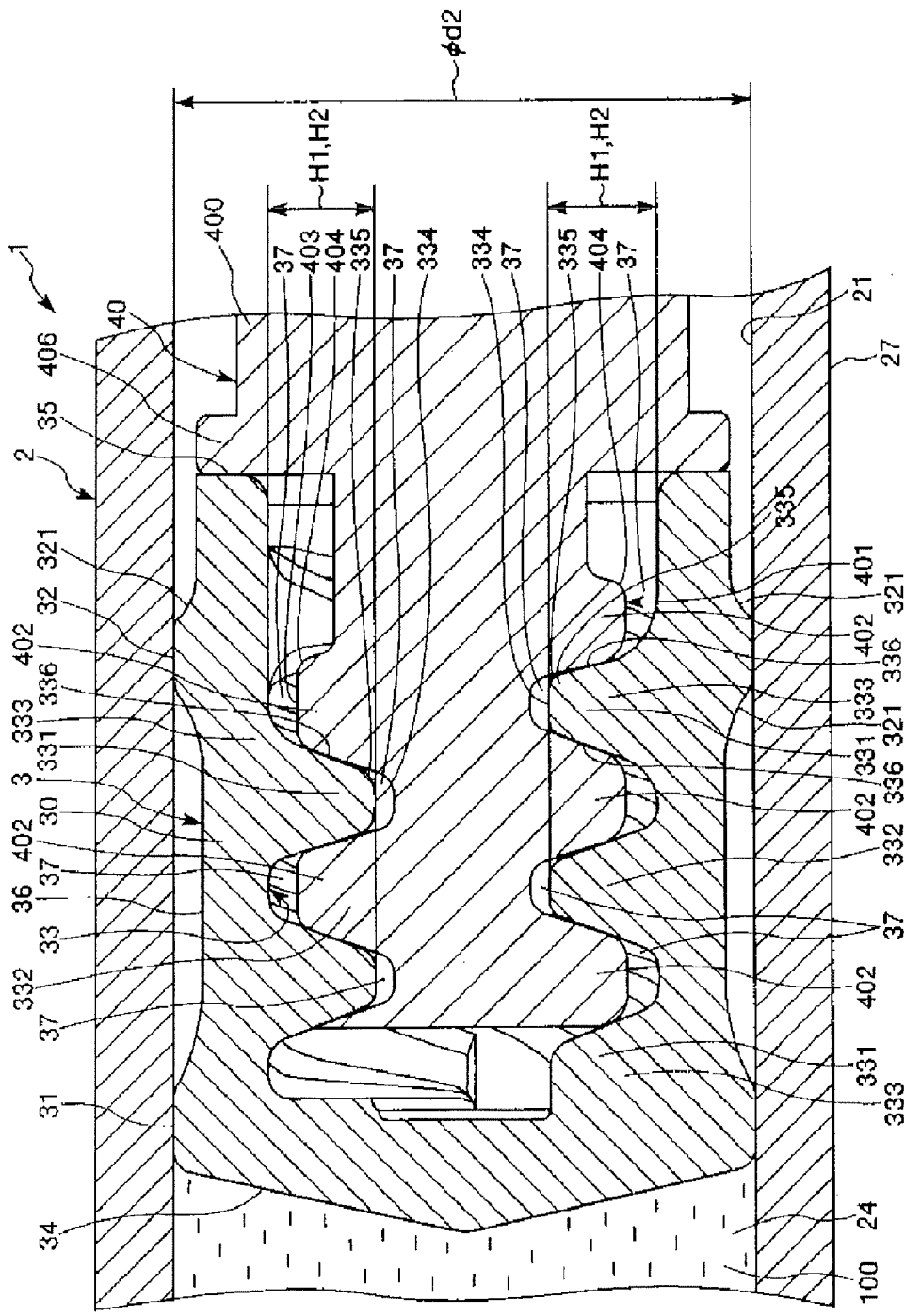
FIG. 3 is a longitudinal sectional view of the gasket according to the present invention, in an inserted state.

FIG. 1 is a partial longitudinal sectional view showing a case where the syringe according to the present invention is applied to a prefilled syringe, FIG. 2 is a longitudinal sectional view of the gasket according to the present invention in an uninserted state, and FIG. 3 is a longitudinal sectional view of the gasket according to the present invention in an inserted state. Incidentally, in the following, for convenience of description, the right side in FIGS. 1 and 2 will be referred to as "a proximal end (side)," and the left side as "a distal end (side)."

The prefilled syringe (hereinafter referred to simply as "a syringe") 1 shown in FIG. 1 has a medicinal liquid 100 preliminarily contained in the inside (inner cavity part 24) of the syringe 1. The syringe 1 includes a syringe outer tube 2, a gasket 3 inserted in the inner cavity part 24 of the syringe outer tube 2, a pusher (plunger rod) 40 operable to move the gasket 3, a lock adaptor (connection member) 23 provided at a distal end portion (mouth section 22) of the syringe outer tube 2, a cap 25 which is put into screw engagement with the lock adaptor 23, and the medicinal liquid 100 filling a space (inner cavity part 24) defined by the syringe outer tube 2 and the gasket 3.

The syringe outer tube 2 includes a bottomed tube-like member having a bottom section 211. The syringe outer tube 2 preferably has an inside diameter of 7 mm or less, more preferably in the range of 3 to 6 mm. Thus, generally speaking, the syringe 1 can be said to be small in diameter.

The bottom section 211 of the syringe outer tube 2 is integrally formed in its central area with the mouth section 22 which is reduced in diameter, relative to a barrel section of the syringe outer tube 2.

The mouth section 22 is formed therein with a passage 221 permitting the medicinal liquid 100 to pass therethrough. The passage 221 communicates with the inner cavity part 24 of the syringe outer tube 2.

Incidentally, an outer peripheral surface 27 of the syringe outer tube 2 is provided with graduations (not shown) for indicating the amount of the medicinal liquid 100 in the inner cavity part 24.

The cap 25 includes a bottomed tube-like member, which is provided on its outer peripheral surface with a male screw (not shown) for screw-engagement with a female screw of the lock adaptor 23.

Engagement of the male screw on the cap 25 with the female screw in the lock adaptor 23 results in connection of the cap 25 and the lock adaptor 23 to each other, or mounting of the cap 25 onto the mouth section 22 of the syringe outer tube 2. As a result of this, a distal end opening of the mouth section 22 can be sealed off, so that the contained medicinal liquid 100 can be prevented from leaking via the distal end opening of the mouth section 22.

In the syringe outer tube 2 as above-mentioned, the gasket 3 made of an elastic material is contained (inserted). The gasket 3 can be slid within the syringe outer tube 2 by operating the pusher 40 along the longitudinal direction thereof. The configuration of the gasket 3 will be described later.

To the gasket 3, the pusher 40 is connected, the pusher 40 being operated to move the gasket 3 in its longitudinal direction within the syringe outer tube 2.

The pusher 40 has a main body section 400. The main body section 400 includes a member which is cross-shaped in cross-section. In addition, the main body section 400 is formed with a male screw 401 on an outer peripheral portion of the distal end thereof. Engagement of the male screw 401 of the main body section 400 (the pusher 40) with the female screw 33 in the gasket 3 results in connection between the pusher 40 and the gasket 3. In addition, as shown in FIG. 3, screw threads 402 of the male screw 401 are uniform in height.

The main body section 400 is formed with a flange-shaped finger rest section 405 at the proximal end thereof. With a finger or fingers put on a distal end surface or proximal end surface of the finger rest section 405, the pusher 40 is pulled in the proximal end direction or pushed in the distal end direction.

As materials for the syringe outer tube 2 (inclusive of the lock adaptor 23) and the cap 25, there can be used, for example, various rigid resin materials, various glass materials, etc. In addition, the material for the syringe outer tube 2 is substantially transparent, for securing visibility of the inside thereof.

In addition, examples of the material for forming the gasket 3 include various rubber materials (particularly vulcanized ones) such as natural rubber, isoprene rubber, butadiene rubber, styrene-butadiene rubber, butyl rubber, etc. and various thermoplastic elastomers based on styrene, polyolefin or the like, which can be used either singly or as a mixture of two or more of them.

Besides, as the medicinal liquid 100, there can be used various medicinal liquids, diagnostic drugs, etc. Examples of which include electrolyte correction injections such as sodium chloride, potassium lactate, etc., vitamin preparations, vaccines, antibiotic injections, steroids, proteolytic enzyme inhibitors, lipid emulsions, various protein products, carcinostatic agents, anesthetics, stimulants, and narcotics.

Now, the gasket 3 will be described in detail below referring to FIGS. 2 and 3.

As shown in FIGS. 2 and 3, the gasket 3 includes a cylindrical gasket body 30 having an inner cavity, and a first projection 31 and a second projection 32 which are projectingly formed on an outer peripheral portion 36 of the gasket body 30. The gasket 3 is made of the above-mentioned elastic material, and can be produced by molding, for example.

The gasket body 30 has, at a distal end portion thereof, a tapered section 34 which is tapered such that the outside diameter gradually decreases in the distal end direction.

A proximal end face 35 of the gasket body 30 is formed with a recess portion opening in the proximal end face, and an inner peripheral surface of the recess is provided with a female screw 33 to be described later.

Incidentally, in this embodiment, the outer peripheral portion 36 of the gasket body 30 has a configuration in which the outside diameter φd3 of a portion 361 on the distal end side relative to the second projection 32 and the outside diameter φd4 of a portion 362 on the proximal end side relative to the second projection 32 are different from each other, but the present invention is not limited to this configuration. In the configuration shown in FIG. 2, the outside diameter φd3 is set to be smaller than the outside diameter φd4.

The outer peripheral portion 36 of the gasket body 30 is provided with the first projection 31 and the second projection 32. The first projection 31 and the second projection 32 make firm contact with an inner peripheral surface 21 of the syringe outer tube 2, whereby liquid-tightness (gas-tightness) can be securely maintained.

In the gasket 3, the first projection 31 is disposed at a most distal portion of the gasket body 30, and the second projection 32 is disposed on the proximal end side relative to the first projection 31 and at an intermediate position (in the vicinity of the proximal end portion) in the axial direction of the gasket body 30. In other words, the first projection 31 and the second projection 32 are disposed to be spaced from each other along the axial direction of the gasket body 30. Incidentally, the spacing distance between the first projection 31 and the second projection 32 is preferably 1 to 10 mm, more preferably 2 to 6 mm.

With the first projection 31 and the second projection 32 thus spaced from each other, the gasket 3 is stably supported within the syringe outer tube 2. More specifically, the axis of the gasket 3 can be prevented from being inclined relative to the axis of the syringe outer tube 2. This enables the gasket 3 to be operated to move smoothly and reliably.

In addition, each of the first projection 31 and the second projection 32 has a projecting ring-like shape extending along the circumferential direction of the outer peripheral portion 36 of the gasket body 30. The first projection 31 and the second projection 32 are so configured that, in an uninserted state in which the gasket 3 is not yet inserted in the syringe outer tube 2 (the state shown in FIG. 2), the outside diameter φd1 of those portions of the gasket 3 which have the first projection 31 and the second projection 32 is preferably greater than the inside diameter φd2 of the syringe outer tube 2 by 3 to 20%, more preferably 4 to 15%. For example, in the case where the outside diameter φd1 is 5.3 mm, the inside diameter φd2 can be 4.9 mm.

With the outside diameter φd1 thus set to be greater than the inside diameter φd2, in an inserted state in which the gasket 3 is inserted in the syringe outer tube 2 (the state shown in FIG. 3), the first projection 31 and the second projection 32 are pressed by the inner peripheral surface 21 of the syringe outer tube 2 against the elastic force of the gasket 3 itself. This ensures that the first projection 31 and the second projection 32 assuredly make firm contact with the inner peripheral surface 21 of the syringe outer tube 2, so that the liquid-tightness of the inside of the syringe outer tube 2 can be maintained more reliably.

As above-mentioned, the gasket body 30 is formed with the female screw 33 at an inner peripheral portion thereof. The female screw 33 is a part with which the male screw 401 of the pusher 40 screw-engages. The engagement between the female screw 33 of the gasket 3 and the male screw 401 of the pusher 40 is performed until a flange section 406 of the pusher 40 comes into contact with the proximal end face 35 of the gasket 3, whereby the gasket 3 and the pusher 40 are connected to each other.

In this embodiment, the female screw 33 is formed between the first projection 31 and the second projection 32.

As shown in FIG. 2, in the uninserted state, the height H1 of the screw thread 331 at a portion on the inner side of the gasket and in close proximity to each of the first projection 31 and the second projection 32 is smaller than the height H2 of the screw thread 332 at another portion. Here, the expression "the screw thread at a portion on the inner side of the gasket and in close proximity to the projection" means a screw thread of the female screw 33 overlapping with the projection across the outer peripheral portion 36 in side view, inclusive of a screw thread having a part at which a foot portion 321 of the projection and a foot portion 336 of the screw thread of the female screw 33 overlap with each other (an intersection part 333 at which the foot portions intersect with each other).

When the gasket 3 having the female screw 33 as above is inserted into the syringe outer tube 2 via a proximal end opening 26 of the syringe outer tube 2, the inserted state as shown in FIG. 3 is established. In this inserted state, the second projection 32 (and the first projection 31, as well) is pressed by the inner peripheral surface 21 of the syringe outer tube 2 toward the center axis side of the syringe outer tube 2. As the result of pressing of the second projection 32, the intersection part 333 is deformed, whereby the height H1 is increased to be equal to the height H2. Consequently, in the female screw 33, the screw threads 331, 332 become uniform in height.

Meanwhile, if the gasket 3 is so configured that the height H1 of the screw thread 331 of the female screw 33 and the height H2 of the screw thread 332 thereof are equal to each other (namely, the screw threads 331, 332 are uniform in height) in the uninserted state, putting of the gasket 3 into the inserted state would cause the first projection 31 and the second projection 32 to be pressed by the inner peripheral surface 21 of the syringe outer tube 2 as above-mentioned, and as the result of the pressing, the height H1 would be increased so as to exceed the height H2. Then, turning the pusher 40 about its axis in an attempt to connect the pusher 40 to the gasket 3 in the inserted state would cause the screw threads 402 of the pusher 40 and the screw threads 331 of the gasket 3 to excessively engage (mesh) with each other, so that the gasket 3 would be turned together with the pusher 40. This results in such troubles as deformation (e.g., twisting) of the gasket 3, generation of an interspace between the inner peripheral surface 21 of the syringe outer tube 2 and the first and second projections 31, 32 of the gasket 3 due to the deformation, leakage of the medicinal liquid 100 and breakage of sterility of the inside due to the generated interspace, and so on.

On the other hand, as above-mentioned, the gasket 3 according to the present invention is so designed that the difference in height between the screw threads 331 and 332 reliably approaches zero in the inserted state shown in FIG. 3, in consideration of pressing of the first projection 31 and the second projection 32. This ensures that when the pusher 40 is turned about its axis in order to connect the pusher 40 to the gasket 3 in the inserted state, the screw threads 402 of the pusher 40 and the screw threads 331 of the gasket 3 engage with each other appropriately; in other words, an appropriate clearance (gap) 37 is formed between the screws. Consequently, the gasket 3 is prevented from being turned, and the gasket 3 and the pusher 40 screw-engage with each other reliably. Thus, in the gasket 3, the above-mentioned troubles are reliably prevented from occurring, and, therefore, the operation of connecting the pusher 40 can be carried out easily.

In addition, the screw threads 402 of the pusher 40 and the screw threads 331 of the gasket 3 firmly mesh with each other to such an extent that unintended disengagement of the pusher 40 from the gasket 3 is prevented from occurring. Consequently, the pusher 40 and the gasket 3 are firmly connected to each other.

Further, the screw threads 331 and 332 of the female screw 33 are each formed with a rounded peak portion 335 at a crest 334 thereof. On the other hand, as shown in FIG. 3, each of the screw threads 402 of the male screw 401 on the pusher 40 is also formed with a rounded peak portion 404 at a crest 403 thereof. This ensures that, at the time of engaging the female screw 33 of the gasket 3 and the male screw 401 of the pusher 40 with each other by turning the pusher 40 about its axis, the operation can be carried out easily.

The difference between the height H1 of the screw thread 331 and the height H2 of the screw thread 332 in the uninserted state is preferably in the range of, for example, 0.08 to 0.30 mm, more preferably 0.10 to 0.24 mm, though the preferable range depends on the amount of deformation of each intersection part 333. This assuredly makes the screw threads 331 and 332 uniform in height in the inserted state.

Further, in the uninserted state, the tooth thickness of the screw thread 331 is greater than the tooth thickness of the screw thread 332. Owing thereto, the angle of the foot portion 336 of the screw thread 331 on the gasket 3 is made constant, whereby close contact of the foot portion 336 with the foot portion of the screw thread 402 of the pusher 40 is achieved, so that friction between the foot portion 336 of the gasket 3 and the foot portion of the pusher 40 is increased. As a result, it becomes difficult to turn the pusher 40 in a disengaging direction, so that disengagement of the pusher 40 is prevented. Incidentally, the difference in tooth thickness is preferably in the range of 0.05 to 0.20 mm, for example. The method for measuring the tooth thickness is not specifically restricted; for example, a sector span method, a method by tooth pressure slide calipers, and the like can be used.

The pitch P of the female screw 33 is not particularly limited, and it is preferably in the range of 1.0 to 4.0 mm, for example. This ensures that the female screw 33 of the gasket 3 and the male screw 401 of the pusher 40 are engaged with each other easily and assuredly, so that the gasket 3 and the pusher 40 are firmly connected to each other.

The gasket and the syringe according to the present invention have been described above referring to the embodiment shown in the drawings. However, the invention is not limited to the above embodiment. The components of the gasket and the syringe can be replaced by those of arbitrary configurations that exhibit the same or similar functions to the above embodiment. Also, arbitrary structures may be added.

In addition, the gasket is not restricted to the above embodiment in which the gasket has the two projections. For example, the gasket may be formed with three or more projections.

Further, in the gasket of the above embodiment, the screw thread located at a portion on the inner side of the gasket and in close proximity to the projection located on the most distal side is also small in height in the uninserted state. However, the present invention is not limited to the above; for example, this screw thread may be large in height.

INDUSTRIAL APPLICABILITY

The gasket according to the present invention which is connected to a pusher having a male screw formed on an outer peripheral portion of a distal end thereof by screw engagement with the male screw of the pusher, the gasket being slid within a syringe outer tube by operation of the pusher in longitudinal directions thereof, the gasket including: a gasket body having a hollow section and a female screw formed on an inner peripheral portion of the hollow section, the female screw being screw-engaged with the male screw; and a plurality of projections which are projectingly formed on an outer peripheral portion of the gasket body so as to extend in a circumferential direction of the outer peripheral portion and which are arranged so as to be spaced from each other along an axial direction of the gasket body, wherein in an uninserted state in which the gasket is not yet inserted into the syringe outer tube, a screw thread located at a portion on the inner side of the gasket and in close proximity to each of the projections has a smaller height than a screw thread located at another portion. Therefore, in the uninserted state, the female screw is characterized in that the screw thread at the portion on the inner side of the gasket and in close proximity to the projection has a smaller height than the screw thread located at the other portion. In the inserted state in which the gasket having such a female screw is inserted into the syringe outer tube, each of the projections is pressed by the inner peripheral surface of the syringe outer tube. According to the extent of the pressing of the projection, the screw thread having the smaller height is increased in height to have the same height as the screw thread having the larger height.

Meanwhile, if the screw threads of the gasket are uniform in height in the uninserted state, putting of the gasket into the inserted state would cause each of the projections to be pressed as above-mentioned, and, according to the extent of the pressing, a condition would be generated in which the screw thread protrudes at a certain position. Then, in this condition, turning the pusher about its axis in an attempt to connect the pusher to the gasket would cause the screw thread of the male screw on the pusher and the screw thread of the female screw in the gasket to excessively engage with each other, so that the gasket would be turned together with the pusher. This results in such troubles as deformation (e.g., twisting) of the gasket, generation of an interspace between the inner surface of the syringe outer tube and the projections of the gasket due to the deformation, breakage of sterility of the inside due to the generated interspace, and so on.

On the other hand, as above-mentioned, the gasket according to the present invention is so designed that the screw thread is uniform in height in the inserted state. This ensures that when the pusher is turned about its axis in order to connect the pusher to the gasket in the inserted state, the screw thread of the male screw on the pusher and the screw thread of the female screw in the gasket engage with each other appropriately. As a result, the gasket is prevented from being turned, and the gasket and the pusher screw-engage with each other reliably. Thus, the above-mentioned troubles are reliably prevented from occurring, and, therefore, the operation of connecting the pusher can be carried out easily.

In addition, the screw thread of the male screw on the pusher and the screw thread of the female screw in the gasket are in mesh with each other assuredly to such an extent that unintended disengagement of the pusher from the gasket is prevented from occurring. This ensures firm connection of the pusher and the gasket to each other.

Therefore, the gasket according to the present invention has industrial applicability.

The invention claimed is:

1. A gasket which is connected to a pusher having a male screw formed on an outer peripheral portion of a distal end thereof, by screw engagement with the male screw of the pusher, the gasket being slid within a syringe outer tube by operation of the pusher in longitudinal directions thereof, the gasket comprising:

a gasket body having a hollow section and a female screw formed on an inner peripheral portion of the hollow section, the female screw being screw-engaged with the male screw; and a plurality of projections which are projectingly formed on an outer peripheral portion of the gasket body so as to extend in a circumferential direction of the outer peripheral portion and which are arranged so as to be spaced from each other along an axial direction of the gasket body, wherein in an uninserted state in which the gasket is not yet inserted into the syringe outer tube, a screw thread located at a portion on the inner side of the gasket and in close proximity to each of the projections has a smaller height than a screw thread located at another portion, wherein, in an inserted state in which the gasket is inserted into the syringe outer tube, each of the projections is pressed by an inner peripheral surface of the syringe outer tube, so that a height difference between the screw threads of the female screw approaches zero, and wherein, in the inserted state, the gasket is connected to the pusher and a clearance is formed between the female screw and the male screw after the pusher has been inserted into the gasket.

2. The gasket according to claim 1, wherein the height difference between the screw threads of the female screw in the uninserted state is of 0.08 to 0.30 mm.

3. A syringe provided with the gasket according to claim 2, wherein the inside diameter of the syringe outer tube is equal to or less than 7 mm.

4. The gasket according to claim 1, wherein the female screw has a pitch of 1.0 to 4.0 mm.

5. A syringe provided with the gasket according to claim 4, wherein the inside diameter of the syringe outer tube is equal to or less than 7 mm.

6. The gasket according to claim 1, wherein in the uninserted state, the outside diameter of a portion of the gasket that has the projection is greater than the inside diameter of the syringe outer tube by 3 to 20%.

7. A syringe provided with the gasket according to claim 6, wherein the inside diameter of the syringe outer tube is equal to or less than 7 mm.

8. A syringe provided with the gasket according to claim 1, wherein the inside diameter of the syringe outer tube is equal to or less than 7 mm.

9. The gasket according to claim 1, wherein the screw thread located at the portion on the inner side of the gasket and in close proximity to each of the projections has a smaller radial dimension from the inner side of the gasket than a screw thread located at another portion, and wherein in the inserted state in which the gasket is inserted into the syringe outer tube, each of the projections is pressed by the inner peripheral surface of the syringe outer tube, so that a difference in the radial dimensions between the screw threads of the female screw approaches zero.

10. A gasket which is connected to a pusher having a male screw formed on an outer peripheral portion of a distal end thereof, by screw engagement with the male screw of the pusher, the gasket being slid within a syringe outer tube by operation of the pusher in longitudinal directions thereof, the gasket comprising:

a gasket body having a hollow section and a female screw formed on an inner peripheral portion of the hollow section, the female screw being screw-engaged with the male screw; and a plurality of protections which are proiectingly formed on an outer peripheral portion of the gasket body so as to extend in a circumferential direction of the outer peripheral portion and which are arranged so as to be spaced from each other along an axial direction of the gasket body, wherein in an uninserted state in which the gasket is not yet inserted into the syringe outer tube, a screw thread located at a portion on the inner side of the gasket and in close proximity to each of the protections has a smaller height than a screw thread located at another portion, wherein, in an inserted state in which the gasket is inserted into the syringe outer tube, each of the projections is pressed by an inner peripheral surface of the syringe outer tube, so that a height difference between the screw threads of the female screw approaches zero, and wherein in the female screw in the uninserted state, the tooth thickness of the lower screw thread is larger than the tooth thickness of the higher screw thread.

11. A syringe provided with the gasket according to claim 10, wherein the inside diameter of the syringe outer tube is equal to or less than 7 mm.

* * * * *